(12) United States Patent
Kuhn

(10) Patent No.: US 7,448,869 B2
(45) Date of Patent: Nov. 11, 2008

(54) MEDICAL OR DENTAL TOOL HOLDER COMPRISING A MULTI-STEP TRANSMISSION ARRANGEMENT

(75) Inventor: Bernhard Kuhn, Biberach (DE)

(73) Assignee: Kaltenbach & Voigt GmbH, Biberach (DE)

( * ) Notice: Subject to any disclaimer, the term of this patent is extended or adjusted under 35 U.S.C. 154(b) by 220 days.

(21) Appl. No.: 10/536,789

(22) PCT Filed: Nov. 21, 2003

(86) PCT No.: PCT/EP03/13089

§ 371 (c)(1),
(2), (4) Date: Nov. 14, 2005

(87) PCT Pub. No.: WO2004/047664

PCT Pub. Date: Jun. 10, 2004

(65) Prior Publication Data

US 2006/0121412 A1    Jun. 8, 2006

(30) Foreign Application Priority Data

Nov. 26, 2002    (DE)    ................ 102 55 120

(51) Int. Cl.
*A61C 1/02* (2006.01)

(52) U.S. Cl. .................................................. 433/105

(58) Field of Classification Search ............. 433/105, 433/114, 126

See application file for complete search history.

(56) References Cited

U.S. PATENT DOCUMENTS

| 4,222,738 A | 9/1980 | Strohmaier ................ 433/105 |
| 5,569,034 A | 10/1996 | Meller et al. ............... 433/105 |
| 5,993,454 A | 11/1999 | Longo ......................... 606/80 |
| 2004/0048711 A1* | 3/2004 | Lev et al. ................... 475/159 |

FOREIGN PATENT DOCUMENTS

| DE | 1 294 591 | 5/1969 |
| DE | 27 17 013 | 10/1978 |
| DE | 42 21 403 C2 | 1/1994 |
| DE | 198 43 951 A1 | 12/1999 |
| EP | 689 802 A1 | 1/1996 |
| FR | 2 530 454 | 1/1984 |

OTHER PUBLICATIONS

International Search Report in PCT/EP2003/013089 dated Mar. 2, 2004.

* cited by examiner

*Primary Examiner*—Melba Bumgarner
(74) *Attorney, Agent, or Firm*—Marshall, Gerstein & Borun LLP

(57) ABSTRACT

In medical or dental handpiece having a treatment tool driven by means of a drive part via a transmission arrangement, the transmission arrangement contains at least two planetary transmission stages connected one after another, which each have a sun gear mounted on a drive shaft, a planetary gear carrier having a plurality of uniformly distributed planetary gears cooperating with the sun gear, and a hollow gear, fixed to a housing, surrounding the planetary gears, having an inner toothing, wherein the planetary gear carrier of at least one transmission stage serves as drive shaft and carrier of the sun gear of the following transmission stage. In order to increase the stability of the arrangement the drive shaft for each transmission stage is extended beyond the sun gear driven thereby and in that the planetary gear carrier belonging to this sun gear is arranged rotatably on the extension.

23 Claims, 2 Drawing Sheets

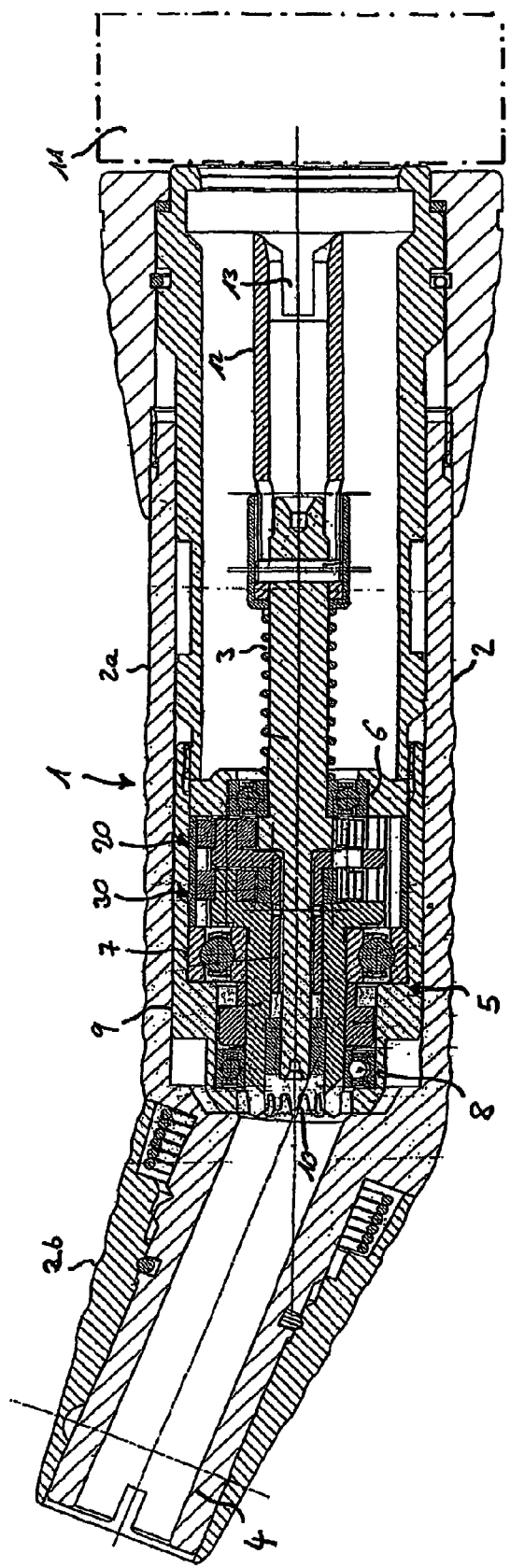
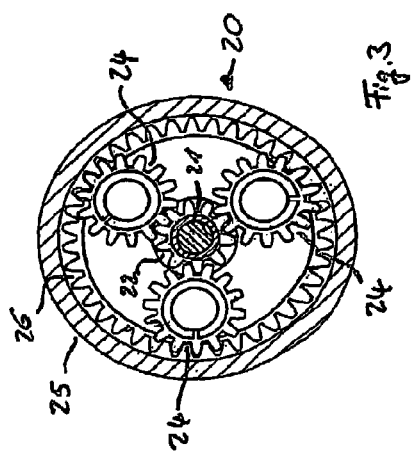

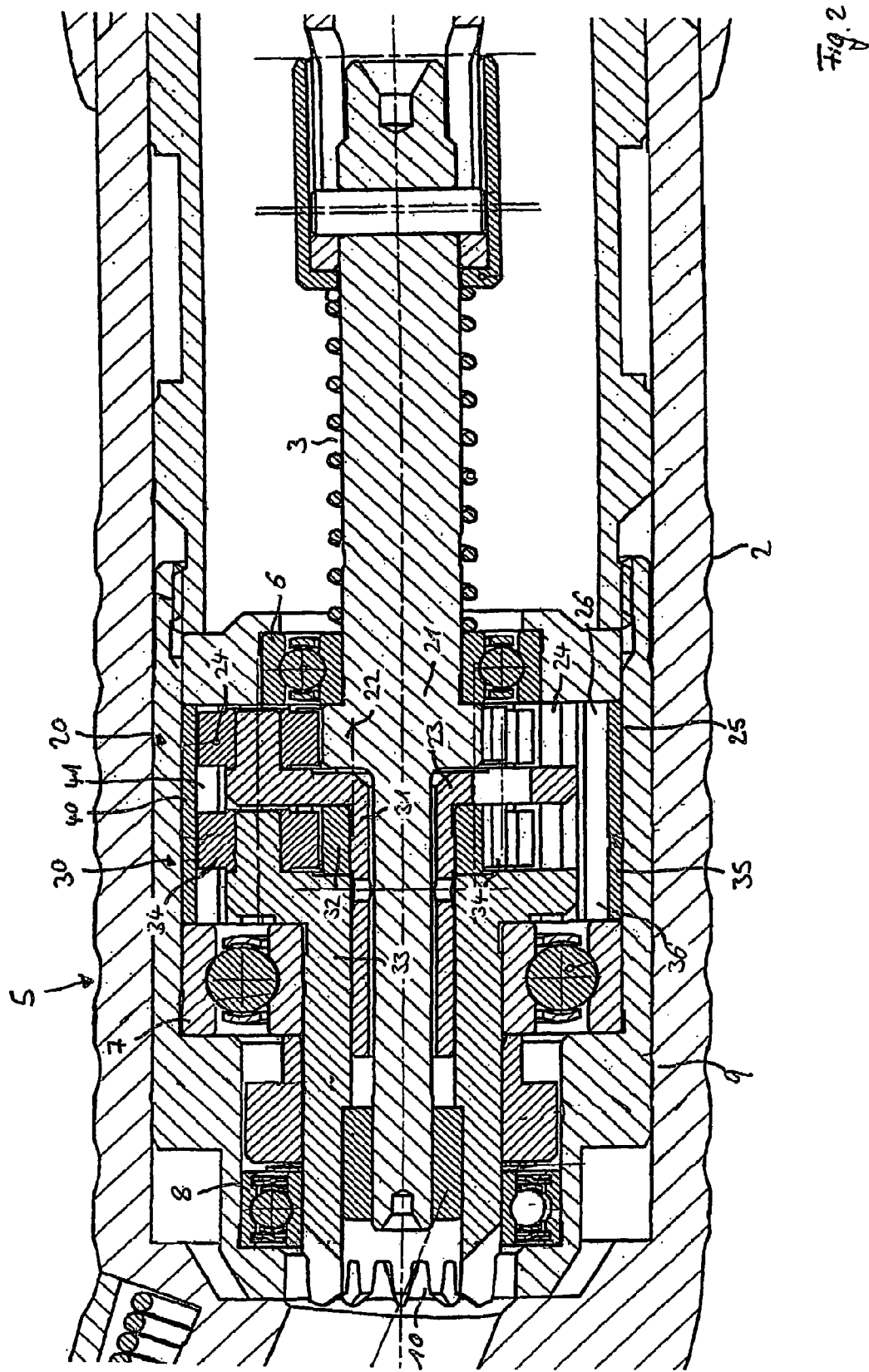

MEDICAL OR DENTAL TOOL HOLDER COMPRISING A MULTI-STEP TRANSMISSION ARRANGEMENT

BACKGROUND OF THE INVENTION

1. Field of the Disclosure

The invention relates to a medical or dental handpiece which has a multi-stage transmission arrangement with at least two planetary gear transmissions connected one after the other, in particular a dental surgical handpiece for emplacing and removing implants.

2. Related Technology

In the case of medical and in particular dental treatment instruments there is often desired a rapid movement, in particular a high speed of rotation of the treatment tool. Dental drills, for example, achieve in use as a rule 30,000 revolutions per minute and more. These high rotary speeds are attained by means of an appropriate configuration of the electric or pneumatic motors. Alongside this, however, there are also kinds of treatments with which significantly lesser rotary speeds are desired for the treatment tool. If, for example, dental implants are to be placed in the jaw or removed, although high torques up to 30 Ncm are needed, however, only rotary speeds in the range of 4000 to 5000 revolutions per minute are needed.

In order to be able to employ the electric or pneumatic motors normally provided at dental work stations also for these kinds of treatment, there are put to use handpieces which have a transmission arrangement for stepping down the drive speed of rotation at the motor. These so-called step-down transmissions can be realized in various manners, however, preferably so-called planetary transmissions are employed, which make possible a particularly good transfer of the power flux. A dental handpiece having a planetary transmission is for example known from DE 42 21 403 C2.

The stepping down of the speed of rotation via a single planetary transmission is, while retaining optimal force transfer, possible only up to a certain degree. In order to obtain a step down of the speed of rotation going beyond this, it is known from U.S. Pat. No. 5,569,034 to form a multi-stage transmission arrangement of a plurality of planetary transmissions connected one after the other. With this known arrangement, the planetary gear carrier of one transmission stage forms the drive shaft for the next following transmission stage, so that a many-fold reduction of speed of rotation is made possible, depending upon the number of transmission stages connected one after the other. FR 2 530 454 A1 also describes a dental handpiece having two planetary transmissions connected one after another.

With the arrangement of U.S. Pat. No. 5,569,034 the individual transmission stages are in each case formed by identical components, whereby at the output end of one component the planetary gear carrier projects and carries on its outside the sun gear for the next following transmission stage. Upon putting together of the overall transmission arrangement, one transmission stage is then placed on the other, whereby the projecting planetary gear carrier of one stage engages in each case into the rearward end of the next stage.

GENERAL DESCRIPTION OF THE INVENTION

Starting from the arrangement known from U.S. Pat. No. 5,569,034, the invention provides a medical or dental handpiece with a transmission arrangement having a plurality of planetary transmissions, whereby the transmission arrangement manifests improved characteristics with regard to its smoothness of running and stability. Further, a particularly compact and space-saving arrangement is to be made possible.

The handpiece in accordance with the invention has first a transmission arrangement which contains at least two planetary transmissions connected one after another, wherein each planetary transmission has in each case a sun gear mounted on a drive shaft, a planetary gear carrier having a plurality of uniformly distributed planetary gears, cooperating with the sun gear, and a hollow gear, with an inner toothing, surrounding the planetary gears and fixed to a housing, and wherein the planetary gear carrier of at least one transmission stage serves as drive shaft and carrier for the sun gear for the following transmission stage.

In accordance with a first aspect of the invention, the drive shaft for each transmission stage is extended beyond the sun gear driven thereby, and the planetary gear carrier belonging to this sun gear is arranged rotatably on the extension. The interleaved arrangement of the planetary gear carriers thereby obtained, makes possible on the one hand a more compact arrangement of the transmission stages, on the other the axial stability of the transmission arrangement is increased and therewith its smoothness of running.

In the case of an advantageous further development of the inventive concept, the planetary gear carriers of all transmission stages are formed as hollow shafts, whereby the extension of the drive shaft for the first transmission stage extends in substance over the entire length of the transmission arrangement centrally through the openings of the planetary gear carriers. Hereby, the transmission shaft of the first transmission stage forms a central carrier element, which over the entire transmission arrangement in axial direction forms a mounting for the transmission stages, through which the axial stability of the transmission arrangement is further improved. Preferably, the planetary gear carriers are mounted to slide with respect to the drive shafts engaging therein.

In accordance with a second aspect of the invention, the hollow gears for all transmission stages are formed by means of a single sleeve-like component with a correspondingly constituted inner toothing. By means of this solution, there is formed a common outer mounting extending at least over the positions of the various planetary gears, which in turn makes possible an improved axial stability of the transmission arrangement. Also, this inventive concept thus leads to an improvement of the running characteristics of the arrangement. This second solution comes into consideration in particular when the sun gears and the planetary gears of the individual transmission stages respectively have identical dimensions. In this case, the common hollow gear can be formed via a simple cylinder-like component.

In accordance with a further aspect of the invention, the components of a planetary transmission are produced at least in part of a ceramic material, whereby preferably silicon nitride ($Si_3N_4$) is concerned. This material distinguishes itself through its high stability and favourable frictional properties, through which a particularly effective and wear-free force transfer is made possible. In particular the drive shafts and the planetary gear carriers of the transmission stages, and the toothed gears arranged therein, may be of this ceramic material.

Preferably, the transmission arrangement is of two planetary transmissions connected one after another, whereby each transmission stage in each case has a transmission ratio of 3:1.

BRIEF DESCRIPTION OF THE DRAWINGS

Below, the invention will be described in more detail with reference to the accompanying drawings. There is shown:

FIG. 1 an exemplary embodiment of a dental handpiece having a two-stage planetary transmission arrangement in accordance with the invention, in section;

FIG. 2 an enlarged illustration of the transmission arrangement; and

FIG. 3 the arrangement of the components of a transmission stage, in section.

DETAILED DESCRIPTION

The handpiece 1, illustrated in FIG. 1, is of an elongate grip sleeve 2, at the forward end of which a non-illustrated head piece with a treatment tool rotatably mounted therein may be arranged. In the case of the illustrated exemplary embodiment there is concerned a so-called angled piece, i.e. the grip sleeve 2 has a rearward and a forward grip sleeve section 2a, 2b, whereby the forward grip sleeve section 2b is arranged with respect to the rearward somewhat angled and the two grip sleeve sections 2a and 2b are connected with one another in one piece. The transmission arrangement in accordance with the invention could, however, be put to use in the same manner also in the case of a straight handpiece.

The drive of the treatment tool mounted in the head piece is effected via a drive shaft train which is of a rearward drive shaft section 3 arranged in the rearward grip sleeve section 2a and a forward drive shaft section 4 arranged in the forward grip sleeve section 2b. The force transfer between the rearward drive shaft section 3 and the forward drive shaft section 4 is effected via a transmission arrangement 5 which is mounted in a transmission housing 9, formed sleeve-like, by means of three roller bearings 6, 7 and 8, which housing is located in the forward region of the rearward grip sleeve section 2a.

The transmission arrangement 5 serves on the one hand for stepping down the speed of rotation of the rearward drive shaft section 3 and on the other hand for force redirection to the drive shaft section 4 arranged at an angle. The force redirection is effected with the aid of a transfer element 10 arranged at the forward end of the transmission arrangement 5, which cooperates with the rearward end of the forward drive shaft section 4 and forms a so-called angled transmission. This can be attained for example by means of appropriately formed conical toothings on the transfer element 10 and the rearward end of the forward transmission shaft train 4, such as is for example known from DE 42 21 403 C2.

The grip sleeve 2 of the handpiece 1 is connectable with its rearward end with a sole schematically illustrated drive part 11 which contains the motor, e.g. an electric motor. The coupling between the motor or the motor shaft of the drive part 11 and the rearward drive shaft section 3 is effected via an elongate coupling sleeve 12 which has at its rearward end a form-fittingly effective rotary element in the form of an insertion slot 13, which upon bringing together of grip sleeve 2 and drive part 11 is brought into driving connection with the motor or the motor shaft.

The transmission arrangement 5 responsible for the stepping down of the motor speed of rotation consists in the illustrated example of two planetary transmissions 20 and 30 connected one after the other, the structure and arrangement of which will now be explained in more detail with reference to FIGS. 2 and 3.

Each transmission stage 20 or 30 forms a complete planetary transmission and consequently is of a so-called sun gear 22 or 32 mounted on a drive shaft 21 or 31, a planetary gear carrier 23 or 33 having three planetary gears 24 or 34 arranged uniformly distributed and cooperating with the sun gear 22 or 32, and a hollow gear 25 or 35 surrounding the planetary gears 24 or 34 and fixed to a housing. The basic manner of functioning of a planetary transmission is well known and thus will only be briefly summarized below with reference to the first transmission stage 20.

The input side drive shaft 21, which in the case of the first transmission stage 20 corresponds to the extension of the rearward drive shaft section 3, carries the sun gear 22, which is formed as a toothed gear with external toothing. This sun gear 22 is enclosed by three planetary gears 24, likewise formed as toothed gears which with their axes are mounted on the planetary gear carrier 23 and cooperate with the sun gear 22. The planetary gear carrier 23 is itself rotatably mounted with respect to the sun gear 22 or the drive shaft 21, wherein the axes of rotation of the drive shaft 21 and of the planetary gear carrier 23 coincide.

The planetary gears 24 are mounted in a sleeve-like hollow gear 25, which has an internal toothing 26 which cooperates with the teeth of the planetary gears 24. The hollow gear 25 itself is arranged fixed to a housing, so that upon a rotation of the drive shaft 21 and therewith of the sun gear 22 the planetary gears 24 rotate externally around the sun gear 22, which results in an axial rotation of the planetary gear carrier 23.

By means of an appropriate selection of the toothing there is attained a stepping down of the rotary speed of the planetary gear carrier 23 in comparison to the rotary speed of the input side drive shaft 21 and of the sun gear 22. In the present case, the toothings are so selected that the speed of rotation of the planetary gear carrier 23 is reduced to a third of the speed of rotation of the drive shaft 21, i.e. the transmission ratio of this transmission is 3:1. Since the torque transfer is effected via a plurality of engagements between the teeth of the sun gear 22 and of the planetary gears 24, the individual tooth flanks of the toothed gears are loaded less in comparison to other kinds of transmission. The arrangement of the various components of the first transmission stage with respect to one another is illustrated in FIG. 3, with the exception of the planetary gear carrier 23.

In the present case, a second transmission stage 30 is connected after the above-described first transmission stage 20. The planetary gear carrier 23 of the first transmission stage 20 serves in this case at the same time as the drive shaft 31 for the second transmission stage 30 and consequently carries the second sun gear 32. This in turn stands in working connection with three further planetary gears 34 mounted on a second planetary gear carrier 33, which planetary gears in turn cooperate with an outer hollow gear 35 having inner toothing 36. The second transmission stage 30 brings about in turn a stepping down of the speed of rotation to one third, so that the final speed of the planetary gear carrier 33 of the second transmission stage 30 corresponds to one ninth of the rotary speed of the input drive shaft 3. For example if the motor-side drive speed of rotation is 40,000 revolutions per minute, there is thus obtained at the output side of the illustrated transmission arrangement a rotary speed of 4444 revolutions per minute.

The transmission arrangement in accordance with the invention distinguishes itself through two special features, which will be explained below.

In correspondence with the first inventive concept, the two drive shafts 21, 31 for each transmission stage 20, 30—that is the first drive shaft 21 and the first planetary gear carrier 23, which at the same time represents the drive shaft 31 for the second transmission stage 30—are extended beyond their driven sun gear 22, 32, wherein in each case the planetary gear carrier 23, 33 associated with a sun gear 22, 32 is arranged rotatably on the corresponding extension. The two planetary gear carriers 23 and 33 are constituted in this case as hollow shafts with an increasing opening diameter, whereby the extensions of the drive shafts 21 and 31 in each case extend in the axial openings of the planetary gear carriers 22 and 32. As can be understood from the illustration in FIG. 2, through this the two planetary gear carriers 22 and 32 are arranged partially interleaved, which makes possible an improved axial connection of the two transmission stages 20 and 30 and therewith an increased stability of the transmission arrangement 5. At the same time the overall arrangement can be kept very compact. Since the drive shafts 21 and 31 must be able to rotate with respect to the planetary gear carriers 22 and 23, they are in each case mounted slidingly against one another.

In the present case, the first drive shaft 21 is even so far forwardly extended that it extends over the entire length of the transmission arrangement 5, centrally through the openings of the planetary gear carriers 23, 33. The first drive shaft 21 thus forms a forwardly projected bearing pin for the entire transmission arrangement 5, through which a further improved axial stability is attained.

A further feature of the transmission arrangement in accordance with the invention consists in that the two sun gears 22 and 32, due to the same transmission ratio of the two transmission stages 20, 30, have the same size. Since, beyond this, also the respective planetary gears 24 and 34 have the same dimensions, in accordance with the second inventive concept a common hollow gear for both gear stages 20 and 30 can be employed. In the present case, the hollow gears are formed by means of a common sleeve-like component 40 having a correspondingly formed inner toothing 41. This common hollow gear also increases the stability of the overall arrangement, which in turn results in an increased running smoothness of the transmission arrangement.

Since the transmission arrangement 5 is configured very compactly due to the measures in accordance with the invention, it can further be formed as a component unit which can be emplaced as a whole in the handpiece, or removed therefrom. The maintenance of the handpiece is significantly simplified through this.

As materials for the components of the two transmission stages 20 and 30 there is employed at least in part a ceramic material, in particular silicon nitride ($Si_3N_4$). This material distinguishes itself through its high stability and lack of sensitivity with respect to external influences, in particular its chemical resistance.

Since, in comparison to steel, it further has excellent sliding and frictional characteristics, the wear characteristics of the transmission are improved with optimum force transfer. Correspondingly, the arrangement in accordance with the invention distinguishes itself through a compact construction, which at the same time results in an improved axial stability of the overall arrangement. Since through this undesired vibrations are avoided, at the same time the working life of the transmission arrangement is increased.

The invention claimed is:

1. Medical or dental handpiece comprising a treatment tool driven by a drive part via a transmission arrangement, the transmission arrangement comprising:
    first and second transmission stages connected one after another, each of the first and second transmission stages having, a sun gear mounted on a drive shaft, and a planetary gear carrier having a plurality of uniformly distributed planetary gears cooperating with the sun gear, the planetary gear carrier of the first transmission stage serving as a drive shaft and carrier of the sun gear of the second transmission stage; and
    a hollow gear, fixed to a housing, surrounding the plurality of planetary gears of both the first and second transmission stages, the hollow gear having an inner toothing,
wherein
the drive shaft for the first transmission stage extends beyond the sun gear driven by the drive shaft of the first transmission stage and the planetary gear carrier associated with this the sun gear driven by the drive shaft of the first transmission stage is arranged rotatably on a portion of the drive shaft for the first transmission stage that extends beyond the sun gear driven by the drive shaft for the first transmission stage.

2. Medical or dental handpiece according to claim 1, wherein
the planetary gear carriers of the first and second transmission stages are hollow shafts and the portion of the drive shaft for the first transmission stage that extends beyond the sun gear extends substantially over the entire length of the transmission arrangement, centrally through openings formed in the planetary gear carriers.

3. Medical or dental handpiece according to claim 1, wherein
the planetary gear carriers are slidingly mounted with respect to the drive shaft.

4. Medical or dental handpiece according to claim 1, wherein
the sun gears and the planetary gears of the first and second transmission stages have identical dimensions.

5. Medical or dental handpiece according to claim 4, wherein
the hollow gear is formed of a single sleeve-like component having an inner toothing.

6. Medical or dental handpiece according to claim 1, wherein at least one of the handpiece and the transmission arrangement has a respective housing and
the drive shaft for the first transmission stage is mounted by a ball bearing.

7. Medical or dental handpiece according to claim 1, wherein at least one of the handpiece and the transmission arrangement has a respective housing and
the planetary gear carrier of the second transmission stage is mounted by a ball bearing.

8. Medical or dental handpiece according to claim 1, wherein
the planetary gear carriers of the first and second transmission stages each carry three planetary gears.

9. Medical or dental handpiece according to claim 1, wherein
components of the first and second transmission stages at least partially comprise ceramic material.

10. Medical or dental handpiece according to claim 9, wherein
the drive shafts or planetary gear carriers of the first and second transmission stages comprise a ceramic material.

11. Medical or dental handpiece according to claim 9, wherein
the sun gear and the planetary gears comprise a ceramic material.

12. Medical or dental handpiece according to claim 9, wherein
the ceramic material is silicon nitride.

13. Medical or dental handpiece according to claim 1, wherein
the first and second transmission stages each have a transmission ratio of 3:1.

14. Medical or dental handpiece according to claim 1, wherein
the first and second transmission stages are arranged in a sleeve-like transmission housing.

15. Medical or dental handpiece according to claim 14, wherein
the transmission arrangement can be emplaced in the handpiece, or removed therefrom, as a structural unit.

16. Medical or dental handpiece comprising a treatment tool driven by a drive part via a transmission arrangement,
wherein the transmission arrangement comprises first and second planetary transmission stages connected one after another, each of the first and second planetary transmission stages having a sun gear mounted on a drive shaft and a planetary gear carrier having three uniformly distributed planetary gears cooperating with the sun gear; and
a hollow gear fixed to a housing, the hollow gear surrounding the three planetary gears of the first and second planetary transmission stages, and the hollow gear having an inner toothing,
the planetary gear carrier of the first transmission stage serving as drive shaft and carrier of the sun gear of the second transmission stage, the drive shaft of the first transmission stage extending beyond the sun gear of the second transmission stage,
wherein
the hollow gear is formed by a single sleeve-like component having an inner toothing.

17. Medical or dental handpiece according to claim 16, wherein
the sun gears and the planetary gears of the first and second transmission stages have identical dimensions.

18. Medical or dental handpiece according to claim 16 wherein
the planetary gear carrier associated with the sun gear driven by the drive shaft of the first planetary transmission stage is arranged rotatably on a portion of the drive shaft of the first planetary transmission stage that extends beyond the sun gear driven by the drive shaft of the first planetary transmission stage.

19. Medical or dental handpiece according to claim 18 wherein
the planetary gear carriers of the first and second transmission stages are formed as hollow shafts and the drive shaft for the first transmission stage extends substantially over the entire length of the transmission arrangement, centrally through openings of formed in the planetary gear carriers 20. Medical or dental handpiece according to claim 18 wherein
the planetary gear carriers are slidingly mounted with respect to the drive shafts.

21. Transmission arrangement for a medical or dental handpiece, for the production of a drive connection between a drive part and a treatment tool,
the transmission arrangement comprising first and second planetary transmission stages connected one after another, each of the first and second planetary transmission stages having a sun gear mounted on a drive shaft, and a planetary gear carrier having three uniformly distributed planetary gears cooperating with the sun gear; and
a hollow gear fixed to a housing, the hollow gear surrounding the planetary gears of the first and second planetary transmission, and the hollow gear having an inner toothing,
wherein the planetary gear carrier of first transmission stage serves as drive shaft and carrier of the sun gear of the second transmission stage, and
the drive shafts for the first and second transmission stages are extended beyond respective sun gears driven thereby and the planetary gear carrier cooperating with the respective sun gear is arranged rotatably on the respective drive shaft.

22. Medical or dental handpiece according to claim 21, wherein
the planetary gear carriers of the first and second transmission stages are hollow shafts and the drive shaft for the first transmission stage extends substantially over the entire length of the transmission arrangement, centrally through openings formed in the planetary gear carriers.

23. Transmission arrangement for a medical or dental handpiece, for the production of a drive connection between a drive part and a treatment tool,
the transmission arrangement comprising first and second planetary transmission stages connected one after another, each of the first and second planetary transmission stages having a sun gear mounted on a drive shaft, and a planetary gear carrier having three uniformly distributed planetary gears cooperating with the sun gear; and
a hollow gear fixed to a housing, the hollow gear surrounding the planetary gears, and having an inner toothing,
wherein the planetary gear carrier of the first transmission stage serves as drive shaft and carrier of the sun gear of the second transmission stage, and the drive shaft of the first transmission stage extends beyond the sun gear of the first transmission stage,
the hollow gear for the first and second transmission stages is formed by a single sleeve-like component having an inner toothing.

* * * * *